US011052265B2

(12) United States Patent
Long et al.

(10) Patent No.: US 11,052,265 B2
(45) Date of Patent: Jul. 6, 2021

(54) FLUENCE MAP OPTIMIZATION FOR FIELD-IN-FIELD RADIATION THERAPY

(71) Applicants: Troy Long, Fort Worth, TX (US); Alan Nelson, Boise, ID (US)

(72) Inventors: Troy Long, Fort Worth, TX (US); Alan Nelson, Boise, ID (US)

(*) Notice: Subject to any disclaimer, the term of this patent is extended or adjusted under 35 U.S.C. 154(b) by 37 days.

(21) Appl. No.: 16/272,230

(22) Filed: Feb. 11, 2019

(65) Prior Publication Data
US 2020/0254278 A1    Aug. 13, 2020

(51) Int. Cl.
*A61N 5/10*    (2006.01)

(52) U.S. Cl.
CPC ......... *A61N 5/1039* (2013.01); *A61N 5/1028* (2013.01); *A61N 5/1045* (2013.01); *A61N 5/1064* (2013.01); *A61N 5/1071* (2013.01); *A61N 5/1036* (2013.01); *A61N 2005/1061* (2013.01)

(58) Field of Classification Search
CPC .. A61N 5/1039; A61N 5/1028; A61N 5/1045; A61N 5/1064; A61N 5/1071; A61N 5/1036; A61N 2005/1061
USPC .......................................................... 378/65
See application file for complete search history.

(56) References Cited

U.S. PATENT DOCUMENTS

| | | | |
|---|---|---|---|
| 2008/0226022 A1* | 9/2008 | Akino | A61B 6/03 378/15 |
| 2011/0075793 A1* | 3/2011 | Akahori | A61B 6/469 378/8 |
| 2011/0122997 A1* | 5/2011 | Lu | A61N 5/1031 378/65 |
| 2011/0228906 A1* | 9/2011 | Jaffray | A61B 6/032 378/65 |
| 2018/0000438 A1* | 1/2018 | Abe | H04N 5/32 |
| 2018/0193671 A1* | 7/2018 | Chappelow | A61N 5/1049 |
| 2018/0280725 A1* | 10/2018 | Sheng | A61N 5/1047 |
| 2018/0345042 A1* | 12/2018 | Voronenko | A61N 5/1039 |
| 2019/0001152 A1* | 1/2019 | O'Connor | A61N 5/1045 |
| 2019/0022423 A1* | 1/2019 | Dilmanian | A61N 5/1084 |
| 2019/0255362 A1* | 8/2019 | Voronenko | A61B 6/4435 |
| 2020/0185119 A1* | 6/2020 | Stahl | A61N 5/1045 |

* cited by examiner

*Primary Examiner* — Jurie Yun
(74) *Attorney, Agent, or Firm* — John L. Sotomayor

(57) ABSTRACT

Improved radiation therapy with field-in-field multi-leaf collimator, utilizing leaf sequencing Field-in-Field's (FIF) to accurately reproduce the input fluence map or original optimized dose distribution. The number of apertures used is constrained to a user-specified value all the way down to as few as 2 apertures which significantly magnifies the effect of poorly formed apertures. The disclosed invention further includes producing fluence maps with a homogenous dose throughout the treated volume utilizing leaf-sequencing Field-in-Field that reproduces more precise input fluence maps to yield optimized dose distribution.

17 Claims, 8 Drawing Sheets

400

FLUENCE MAP OPTIMIZATION FOR FIELD-IN-FIELD RADIATION THERAPY

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

The current state of art for optimized radiation treatment delivery to patients deals with the settings of radiation treatment systems to reflect the dose protocol as determined by radiation oncologists. In many cases, these protocols require modulating the fluence intensity of a treatment field, which can be modeled as a 2-dimensional fluence intensity map that represents the photon fluence intensity for small subsections of the field. Modern radiation therapy machines have the capability of modulating the actual photon fluence intensity throughout a field of radiation through the use of the multi-leaf collimator (MLC). A treatment plan that delivers a modulated fluence map is called intensity-modulated radiation therapy (IMRT).

Many conventional means exist for translating the ideal fluence map into specific deliverable MLC apertures—a process known as leaf-sequencing. This includes the ability to calculate and analyze the radiation contribution in the patient anatomy from the resulting treatment apertures to be delivered. These conventional means for sequencing, however, are not designed for a limited number (<10) apertures which can be desirable for certain treatment sites and techniques.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

Figure 1:
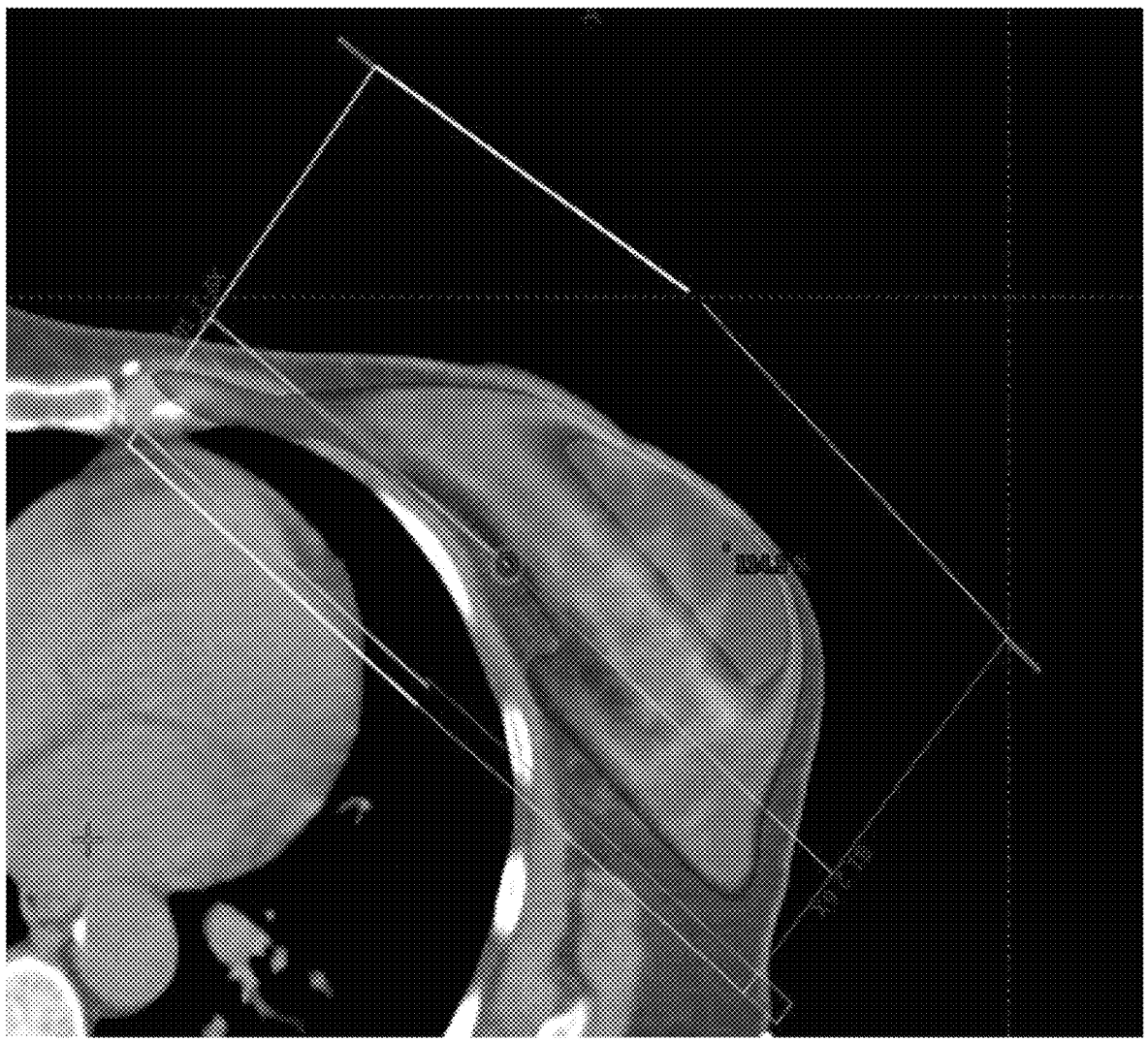
FIG. 1 is a view of a common unbalanced delivery of a radiation dose for cancer treatment consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term, multi-leaf collimator (MLC), is used herein as the means for setting the beam aperture, in the field of radiation therapy delivery. Where MLC is commonly used to create patterns that shape the radiation treatment, which matches target(s) for conformal delivery. In addition, MLC is often used to create an array of beam shapes that create a desired intensity modulation and desired 3D dose distribution. MLC consists of a large number of elongated thin leaves arranged side to side in an array, where each leaf can be moved longitudinally so that its tip can be extended into or withdrawn from the radiation field. MLC is made up of individual leaves that are constructed from a high atomic numbered material, (i.e. tungsten), which can move independently in and out of the path of a particle beam in order to block it. MLC provides conformal shaping of radiotherapy treatment beams. MLC, as used in radiation therapy, improves accuracy and effectiveness of radiation therapy and reduces the time for every treatment dose, compared to previously used conventional shielding for static conformal radiotherapy or 3D-planned dynamic radiotherapy administration.

The term, aperture, as used herein for radiation treatment, refers to a hole or an opening through which light travels, where the aperture further determines the cone angle of a bundle of rays that come to a focus in the image plane. Aperture further refers to controlling and modifying the shape and penetration of photons during treatment of a patient. The devices, incorporating aperture, are typically connected to an output of a radiation source for radiation therapy.

The term, Leaf Sequencing, is used herein to refer to controlling the leaves of an aperture in radiation treatment.

Leaf sequencing allows the delivery of different radiation fluences to different parts of a treatment volume from a single treatment angle. Leaf Sequencing combined with multiple treatment angles makes it possible to better control the amount of radiation delivered to different parts of the treatment volume. Leaf Sequencing further includes, in some embodiments, achieving different radiation fluences by assigning different leaf pairs to define the aperture for irradiating different parts of the treatment volume.

The term, "Intensity-modulated radiation therapy" (IMRT), or similar terms, as used herein, is defined as an advanced mode of high-precision radiotherapy that uses computer-controlled linear accelerators to deliver precise radiation doses to a malignant tumor or specific areas within the tumor, which allows for the radiation dose to conform more precisely to the three-dimensional (3-D) shape of the tumor by modulating, or controlling, the intensity of the radiation beam in multiple small volumes. Further, IMRT utilizes a large number of apertures. (e.g. >20)

The term, Field-in-field (FIF) and associated technique, is used herein to refer to treating multiple fields within a single field opening, when a small number of apertures is used. FIF involves determining aperture shapes and associated intensities at given beam locations that will result in a conformal dose throughout the treatment area. Similar to IMRT, the FIF technique is used to determine apertures and associated intensities for beam locations and angles for automated radiation therapy treatment planning, where the radiation treatment beam is stationary.

The primary distinction between IMRT and the FIF technique is the number of apertures used at each treatment location, where the FIF technique utilizes a small number of apertures per beam. (e.g. 2-6)

The associated algorithm process for the disclosed FIF technique is implemented for each radiation treatment beam independently. The FIF sequencing algorithm addresses the challenge of matching field-in-field dose with fluence map optimization dose(s) by first generating apertures in a beam-independent setup and then optimizing intensities to generate a clinically desirable treatment plan and satisfy the dose objective, where the dose is calculated based on the treatment equipment parameters. The FIF sequencing algorithm is initiated by the input fluence at the pre-process stage. Where for each beam, the preferred leaf closing location is determined by ensuring the specific field is small enough such that span and exposure constraints are not violated by leaves extending across the "closed" rows that have the leaves meet outside of the field. If it is determined that the beam is not in the leaf closing location then the leaves in the flash (i.e. part of the field where the radiation misses the patient body) region are closed (if possible) or the leaf closing is feathered across all apertures (i.e. linearly space leaf closing positions across the field). In addition, fluence stratification which is part of this pre-process stage, involves running a common citable algorithm (i.e. K-means) on beamlets in set with nonzero fluence to generate stratified fluence levels to aid in greedy aperture determination. This results in explicitly ending the algorithm's iterative processing to yield a small number of high-quality apertures, as part of the FIF technique. Also, beamlets that are candidates for causing hot spot doses are identified. Where hot spot candidates are beamlets in whose pencil beam directly intersects voxels that have doses near the max dose from the fluence map optimization. It should be noted that the identified beamlets that may result in hot spot candidate doses are only allowed to be rounded down when stratified. The assumption of beam-independence can be dropped and deviations from desired cumulative dose may be incorporated in between beam sequencings as well.

The FIF sequencing algorithm process commences to iteratively generate the desired apertures for optimized dose distribution. The FIF sequencing algorithm process also estimates an intensity value for each of the current apertures. The FIF sequencing algorithm can estimate the intensity value by either: (1) calculating the intensity value as a product of the minimum value across the intersection of beamlets exposed by the aperture and beamlets; or (2) minimizing square distance from the original fluence for optimized aperture intensity (i.e. a simple least-squares problem); or (3) minimizing squared distance from the original dose for optimized aperture intensity (i.e. fluence map optimization problem). The FIF sequencing algorithm further runs to assess the criteria to determine whether to add apertures, where the assessed aperture criteria are: (1) the aperture will be a feasible, deliverable aperture; or (2) the aperture will be a closed field; or (3) the aperture will have too low of an estimated intensity; or (4) the aperture is the same shape as an existing aperture. If the FIF sequencing algorithm determines (4) is true, then intensity is added to the existing aperture and the loop goes again. If the FIF sequencing algorithm determines (1) is true, the aperture is added and the loop goes again. If the FIF sequencing algorithm determines (2) or (3) is true, then the aperture-adding loop stops. The FIF sequencing algorithm process then determines an overall optimized beam intensity for optimal treatment. This determination, in the present disclosure, recreates the original dose distribution using voxel-based piecewise quadratic penalties. However, any objective can be used in this model. The FIF sequencing algorithm, in making this determination, utilizes objective function weights to balance the clinical preference between hotspot limiting and ensuring target coverage. Further, the parameter(s) associated with determining the optimized beam intensity are calculated by summing the beamlet-based doses from all exposed beamlets in each aperture on beam, in order to yield the beam intensity that results in optimal treatment doses.

The current state of the art does not adequately account for the fact that the treatment area of the patient, and associated tissue, require slightly different levels of radiation depending on a variety of factors regarding said treatment area, and associated tissue, including, at least, the tissue depth and shape of the body surface. As such, there is a need for a system and method that ensures that the cells and tissues within a single patient treatment area receive the highest level of radiation dose to sufficiently treat the affected tissue, without exposing the tissue of the patient's treatment area to excessive radiation, which can potentially harm the patient. Since patient treatment areas often have a variety of tissue depths in the patient treatment area that are often affected at different levels by the disease, there is a need for system and method for determining and delivering the most homogeneous dose distribution across the patient's treatment area that also utilizes the maximum dose to safely and effectively treat each part of the patient's treatment area.

The current invention addresses these previous challenges utilizing leaf sequencing Field-in-Field's (FIF) that accurately reproduces the input fluence map for optimized dose distribution, further where the number of apertures used is constrained to a user-specified value all the way down to as few as 2 apertures. The present invention's combination of utilizing FIF sequencing and strict aperture number limits, which ideally keeps the aperture number below 10, yields a significantly more effective dose distribution to affected tissue areas with varying contours, in a manner that has not been done before and with a degree of effectiveness that results in improved treatment by providing for radiation therapy treatment planning which reduces the need for extensive user interaction, iterative trial-and-error to generate treatment plans and use of excessive radiation energy to achieve adequate treatment outcomes.

In an embodiment, the current invention provides an improved means for optimizing the delivery of dosages in FIF systems utilizing a low number of apertures per beam. In addition, the current invention discloses feathering low level and high-level beams to deliver a radiation dose that is specific to the tissue to which the dose is being delivered and optimizing fluence levels for FIF implementations, in order to produce fluence maps that yield a homogeneous dose throughout the treated volume. The explicit algorithm details for the FIF system and sequencer, includes calculating the dose based on FIF parameters, where said FIF parameters include at least a desired number of apertures on beam, the number of leaf rows on beam, the number of columns on beam, the intensity of beamlet indexed by row and column (determined by Fluence Map Optimization), lower-bounds on aperture intensity, the leaf span limit for each beam, the leaf exposure limit for each beam, the dose received by voxel at unit intensity from beamlet, the stratified fluence at beamlet, the stratified fluence at beamlet that needs to be sequenced, and the optimal dose distribution from fluence map optimization. Further, the described algorithm solves the problem of matching FIF dose(s) with fluence map optimization dose(s), through first generating apertures in a beam-independent setup, then optimizing intensities to satisfy the dose objective and yield a clinically desirable treatment plan.

The current invention discloses a dose estimation algorithm which requires two main inputs: (1) Accurately calculate open field dose and (2) tuning parameters for a Finite-Size-Pencil-Beam (FSPB)-like kernel. The explicit algorithm details for the field-in-field sequencer calculation are described as follows.

Notation

Variables $y_a^b$—intensity of aperture a on beam b $L_{ar}^b$—left leaf position (column number) of aperture a on beam b at row r $R_{ar}^b$—right leaf position (column number, non-inclusive) of aperture a on beam b at row r $z_j$—dose received by voxel j Sets B—set of beam locations V—set of voxels $F_b$—set of feasible leaf positions ($L^b$, $R^b$) for beam b (includes, but not limited to leaf span, exposure, "smell-test" constraints (see below))

$H_b$—set of beamlets (r, c) whose pencil beam hit the tumor (i.e., beamlets in the beam's-eye-view covering the tumor)

Parameters (Vectors Indexed by Subscripts)

$A_b$—desired number of apertures on beam b

This is usually seen as an upper bound $W_b$—number of leaf rows on beam b $C_b$—number of columns on beam b (discretization unit of leaf positioning across rows on beam)

$x_{rc}^b$—intensity of beamlet indexed by row and column (r, c) on beam b as determined by Fluence Map Optimization G—lower bound on aperture intensity $S_b$—leaf span limit for beam b $E_b$—leaf exposure limit for beam b $D_{rc}^b$—Dose received by voxel j at unit intensity from beamlet (r, c) on beam b This is from our dose approximation algorithm. This allows for a fast forward calculation of beamlet-based dose (z=Dx) for the final optimization stage $T_{rc}^b$—Stratified fluence at beamlet (r, c) on beam b (see pre-processing)

$U_{rc}^b$—Stratified fluence at beamlet (r, c) on beam b needed to be sequenced (see pre-processing)

$\bar{z}_j$—optimal dose distribution from fluence map optimization

In an embodiment, the dose calculations are performed by first taking as input the beamlet intensities, as defined above, and the parameters and sets described and included in the algorithm notation above. When solving for the optimized fluence map, for each beam, independently, the pre-processing input fluence and initializing sequencing algorithm are received by the system. Once again for each beam the system iteratively adds apertures until a pre-configured aperture limit is met. This limit may be determined for each treatment regimen. Each beam is then processed for the feasibility and shape for each aperture associated with the beam. Upon completion of processing for each beam, all beams are considered and all apertures are processed to simultaneously adjust intensities because the dose received by the patient is a function of all apertures. The output of the individual beam processing and the collective beam processing is a set of apertures and associated intensities for each beam, represented by the notation of y (aperture intensity), L (Left leaf positions), and R (Right leaf positions).

In an embodiment, the system accounts for Physical leaf constraints in preparing fluence maps. In a non-limiting example where $F_b$ for each aperture a is considered the system contains a Leaf exposure limit. This limit (in number of columns) provides the amount in terms of distance a leaf can extend past the edge of the field, and is defined as:

$$L_{ar}^b \leq E_b \forall r=1, \ldots, W_b, b=1, \ldots, B$$

$$R_{ar}^b \leq C_b - E_b \forall r=1, \ldots, W_b, b=1, \ldots, B$$

A Leaf span limit (in number of columns) provides the distance a leaf position can differ from others on one side of the field. In this non-limiting example, all left leaves must be within this positional distance of each other. This distance is defined as:

$$\max_{r=1,\ldots,W_b}\{L_{ar}^b\} - \min_{r=1,\ldots,W_b}\{L_{ar}^b\} \leq S_b \forall b=1, \ldots, B$$

$$\max_{r=1,\ldots,W_b}\{R_{ar}^b\} - \min_{r=1,\ldots,W_b}\{R_{ar}^b\} \leq S_b \forall b=1, \ldots, B$$

Interdigitation—adjacent leaves from opposing sides cannot overlap. In a non-limiting example of this principal, a row 1 left leaf position<=a row 2 right leaf position as shown:

$$L_{ar}^b < R_{a(r+1)}^b \forall r=1, \ldots, W_b-1, b=1, \ldots, B$$

$$L_{a(r+1)}^b < R_{ar}^b \forall r=1, \ldots, W_b-1, b=1, \ldots, B$$

This constraint is only on some treatment machines

In certain instances, and for certain dose delivery machines, the difference in left leaf position and right leaf position for each row must be nonzero. This condition is referred to as Non-closing leaves. In a non-limiting example, let g be the required gap in number of columns $$g + L_{ar}^b < R_{ar}^b \forall r=1, \ldots, W_b, b=1, \ldots, B$$

This constraint is only on some treatment machines

In an embodiment, an explicit solution to the overall Master problem of exact dose solution for a particular machine set up may be too large to accurately calculate. For this reason, a heuristic solution, where subset calculations are performed, may be created to produce a solution for the machine setup and fluence map. The Master problem may be represented as follows:

$$\min_{y,L,R} f(z)$$

General objective function subject to $z_j = D_j(y, L, R) \forall j$

Dose calculated from machine parameters $(y_a^b, L_a^b, R_a^b) \in F_b \; \forall \; a = 1, \ldots, A_b, b = 1, \ldots, B$ Apertures feasible (see $F_b$ definition)

In this embodiment, $f(z)$ can be any objective function of the dose. In the following algorithm, the system may solve the problem of matching field-in-field dose with fluence map optimization dose, $\bar{z}$, through first generating apertures in a beam-independent setup then optimizing intensities to satisfy that dose objective. The function $D_j(y, L, R)$ is a forward dose calculation based on machine parameters.

This problem as formulated is too large/complicated to solve explicitly, so we use the following process to calculate the solution. The resulting solution is both feasible for the above problem and generates a clinically desirable treatment plan.

Algorithm Process

In an embodiment, for each beam b, the preferred leaf closing location must first be determined. In performing this leaf closing location determination, if the field is small enough such that span and exposure constraints are not violated by leaves extending across the field, then "closed" rows have the leaves meet outside of the field. If span and exposure constraints would be violated by leaves extending across the field, then, if possible, close the leaves in the flash region. If it is not possible to close the leaves in the flash region, then feather the leaf closing across all apertures by, in a non-limiting example, linearly spacing leaf closing positions across the field.

In an embodiment, a very important consideration is the step of Fluence stratification. This may be accomplished by running an available k-means clustering algorithm on beamlets in set $H_b$ with nonzero fluence to generate the stratified fluence at beamlet (r, c) on beam b, as represented by the parameter $T_{rc}^b$. The number of clustering points is at most the number of desired apertures. This step aids in explicitly ending an iterative algorithm with a small number of high-quality apertures. In addition, beamlets with nonzero intensity not in $H_b$ have their $T_{rc}^b$ set as determined in a pre-processing flash step. In the stratification step, beamlets that are candidates for causing hot spot doses in potential delivery fluence maps are only allowed to be rounded down when stratified. In a non-limiting example, hotspot candidates may be defined as beamlets in $H_b$ whose pencil beam directly intersects voxels that have dose near the max dose from the fluence map optimization. A key observation is that beamlets with the highest fluence are not necessarily the beamlets that create worrisome dose hotspots in the end. In an embodiment, rounding influence may also be used to iteratively incorporate cumulative dose influence as compared to the optimal fluence dose and round beamlets up or down to nearest stratification levels accordingly. Each beamlet that has nonzero intensity and is not in $H_b$ will have its intensity fully determined by the first (i.e. open field) aperture.

In an embodiment, the dosage requirements may be evaluated through iterative aperture generation. The iterative aperture generation may be composed of repeated steps beginning while the number of apertures is less than A apertures or until some other break occurs. The system may then set $U_{rc}^b$ equal to the following for all (r, c):

$$U_{rc}^b = \max\left\{ T_{rc}^b - \sum_{a=1}^{A} 1\{L_r \le c < R_r\} y_a^b, 0 \right\}$$

Next to generate beamlet desirability weights, if $U_{rc}^b > 0$, then beamlet desirability is −1. In a non-limiting example, these values may be scaled to 1 for convenience, but these values can be relatively tuned during the iterative process. If instead, $U_{rc}^b$ is some positive value, in this determination, an arbitrarily large value corresponds with a preference to cover beamlets that do not need any more fluence. Alternatively, smaller values allow for some beamlets to be uncovered even if the desired fluence is already achieved.

In an embodiment, the fluence map graph construction and initial leaf determination may consist of steps that provide a readily understandable visual representation of the dose delivery mapping. The general idea is to make a graph that connects row-adjacent (r to r+1) feasible leaf pairs, where the feasibility may be defined by set $F_b$ (Please see http://iopscience.iop.org/article/10.1088/0031-9155/52/24/009/meta). For each row, identify columns where beamlet endpoints could occur. In a non-limiting example, any time $U_{rc}^b < U_{r(c+1)}^b$, add each (r, c±buffer) potential left leaf position and any time $U_{rc}^b > U_{r(c+1)}^b$, add each (r, c±buffer) potential right leaf position for each row. Added to potential leaf positions is a dummy "null" node to avoid infeasibility for a path across the graph that has an arbitrarily high penalty value, such a condition could be represented by a penalty value higher than the sum of all normal nodes. A directed graph may then be constructed where each node represents a particular left-right leaf pair for a particular row. Connecting arcs are connected from each node for a particular row, say row r, to the following row, r+1 if the adjacent row leaf arrangement satisfies the constraints in $F_b$. Row 1, the first row, and row $W_b$, the last row, may be connected to source and sink nodes, respectively. The cost for each arc is the beamlet desirability weight for the node into which the arc is pointing. A common graph algorithm, such as, in a non-limiting example, Dijkstra's algorithm, may be used to solve for the "shortest path" from source to sink, effectively finding the feasible aperture shape that minimizes the opening of undesirable beamlets as determined by the beamlet desirability score. In this non-limiting example, the output of the shortest path is a set of left and right leaf positions.

In an embodiment, the process may be optimized through the steps of aperture smoothing and satisfying global span constraints. The graph solution only explicitly enforces constraints for adjacent rows. This means that there may be two main areas of concern for a deliverable, desirable solution: these areas are presented as (1) undesirable shape characteristics and (2) leaf span. Undesirable shape characteristics—each of the following are corrected by simple heuristics with tuning parameters determined by clinical experts such as the identification of single leaves jutting into the center of an aperture. In a non-limiting example, for each leaf, if the average position of the leaves ±n rows away is significantly different than the leaf in question, set the leaf to the average position between the surrounding leaves that still covers up 0-intensity beamlets. To identify small, discrete areas, if an aperture opening portion is smaller than a particular area, as defined by a clinician, or is smaller than a certain number of rows, or is thinner than a certain number of columns, those leaves are closed to the preferred leaf closing positions.

Undesirable Leaf span conditions may be identified as well. Unless the field width is greater than the span constraint, this does not come into question. However, in larger cases this may occur. Most of the time this constraint is not violated anyway, but in the rare cases where it occurs, may perform the following steps to correct this undesirable condition. Leaf span is side-specific. If the leaves on a particular side present as leaves that are too far apart, then:
1) If leaves can be brought closer together and not cover or expose any beamlets in $U_{rc}^b$, then those changes are made.
2) If not, then the sequencer is rerun with a field opening the same width as the leaf span constraint aligned toward the side with the greater average $U_{rc}^b$.

In an embodiment, intensity determination may consist of estimating an intensity value for the current aperture. While the aperture intensities will be optimized simultaneously in the end, an estimated value is needed to update $U_{rc}^b$. In the following non-limiting examples, there are multiple ways to solve for intensity.
   a) Option 1: The aperture intensity is the minimum value of $U_{rc}^b$ across the intersection of beamlets exposed by the aperture and beamlets in $H_b$
   b) Option 2: Aperture intensity is optimized based on minimizing squared distance from the original fluence. This is a simple least-squares problem.
   c) Option 3: Aperture intensity is optimized based on minimizing squared distance from the original dose. This is a fluence map optimization problem.

In an embodiment, there may be a requirement to add one or more apertures to the solution to optimize the fluence map. In this embodiment, aperture adding criteria may be described as:
   i) At this point, the aperture will:
      a) be a feasible, deliverable aperture
      b) be a closed field
      c) have too low of an estimated intensity
      d) the aperture is the same shape as an existing aperture
   ii) If (d) is true, the intensity is added to the existing aperture and the loop goes again
   iii) If (a) is true, the aperture is added and the loop goes again
   iv) If (b) or (c) is true, then the aperture adding loop stops.

In an embodiment, the Overall Intensity Optimization may be recreated using voxel-based piecewise quadratic penalties. However, any objective can be used in this model. This is a convex model and solved using conventional continuous convex solvers. In this solution, the objective function weights are used to balance the clinical preference between hotspot limiting and ensuring tumor coverage, and the parameter $D_{aj}^b$ is calculated by summing the beamlet-based doses from all exposed beamlets in each aperture a on beam b.

$$\min_{y_a^b} \sum_{j=1}^{V} \alpha_j (z_j - \bar{z}_j)_+^2 + \beta_j (\bar{z}_j - z_j)_+^2$$

$$y_a^b \geq G \ \forall \ a = 1, \ldots, A_b, b = 1, \ldots B$$

$$z_j = \sum_{b=1}^{B} \sum_{a=1}^{A_b} D_{aj}^b y_a^b \ \forall \ j = 1, \ldots, V$$

Dose Estimation

For the dose estimation algorithm, two main inputs are needed. (1) Accurately calculated open field dose and (2) tuning parameters for an FSPB-like kernel. Dose calculation is the process by which a dose distribution is estimated in the body given a set of machine parameters. Due to the nature of the non-homogeneous fluence patterns used in IMRT, electronic compensators, and field-in-field, algorithms need the individual contributions of subsections of the beamlets to specific volume pixels (voxels) inside the body. With such an association, the act of calculating dose is simply a matrix-vector multiplication of these values and beamlet intensities. However, calculating these values explicitly is time consuming. Instead, the open field dose, which can be seen as the aggregate dosimetric effect of all beamlets at unit intensity, can be quickly calculated and used as a basis for dividing up each beamlet's dosimetric effect on each voxel.

General Dose Estimate Algorithm

In an embodiment, for each beamlet, determine a set of voxels within some distance of the beamlet's central axis through the patient where the distance is a tradeoff between speed and accuracy. For each voxel in that set, multiply the distance normalized, tuned beamlet kernel, by depth and off-axis angle, by the open beam voxel dose received.

The beamlet kernels can be trained with any real or simulated data, with the parameters smoothed utilizing linear regression.

Adjustments to Dose Calculation for Apertures

Dose calculation is the process by which a dose distribution is estimated in the body given a set of machine parameters.

The dose for a particular aperture is calculated by summing the aggregate effect of all exposed beamlets in the aperture. A leaf edge leakage penalty is applied to the leaf-covered beamlets, and a falloff term is applied near the leaf tips, both of which are based in the physical characteristics of the leaf material and shape of the leaves. These can be estimated through simulation or through clinical experience.

Further for each beamlet, the general dose estimation algorithm determines a set of voxels within some distance of the beamlet's central axis through the patient. For each voxel in that set, the general dose estimation algorithm will multiply the tuned beamlet kernel by depth and off-axis angle, by the open beam voxel dose received. Wherein the tuned beamlet kernel is normalized by the distance.

Dosing for a particular aperture is calculated by summing the aggregate effect of all exposed beamlets in the aperture. A leaf edge leakage penalty is applied to the leaf-covered beamlets, and a falloff term is applied near the leaf tips, both of which are based in the physical characteristics of the leaf material and shape of the leaves. These can be estimated through simulation or through clinical experience. The beamlet kernels can be trained with any real or simulated data, with the parameters smoothed with linear regression. The kernels have the general shape as seen in the associated Figures. Due to the nature of the non-homogeneous fluence patterns used in IMRT, electronic compensators, and FIF algorithms need the individual contributions of subsections of the beamlets to specific voxels inside the body. With such an association, the act of calculating dose is simply a matrix-vector multiplication of these values and beamlet intensities. However, calculating these values explicitly is time consuming. Instead, the open field dose, which can be seen as the aggregate dosimetric effect of all beamlets at unit intensity, may be quickly calculated and used as a basis for dividing up each beamlet's dosimetric effect on each voxel. In addition, the dose optimization intensity is achieved by recreating the original dose distribution using voxel-based piecewise quadratic penalties, wherein the model is a convex model and may be solved using conventional continuous convex solvers. In a non-limiting example, any dose objective can be used in this model.

Turning now to FIG. 1, this figure presents a view of a common unbalanced delivery of a radiation dose for cancer treatment consistent with certain embodiments of the present invention. In an exemplary embodiment, this figure presents a dose amount delivered to a portion of the human body having a contour with various depths of tissue as currently configured 100. The contour of the human body presents thinner and thicker tissue portions that may receive radiation doses that may be either insufficient or an overdose for the tissue when the radiation dose is not tuned properly for the contouring of the tissues. When a radiation dose is delivered as a constant dose or a poorly configured dose, tissues can be overwhelmed or the treatment can be ineffective based upon the tissue to which the radiation dose is delivered.

Figure 2:
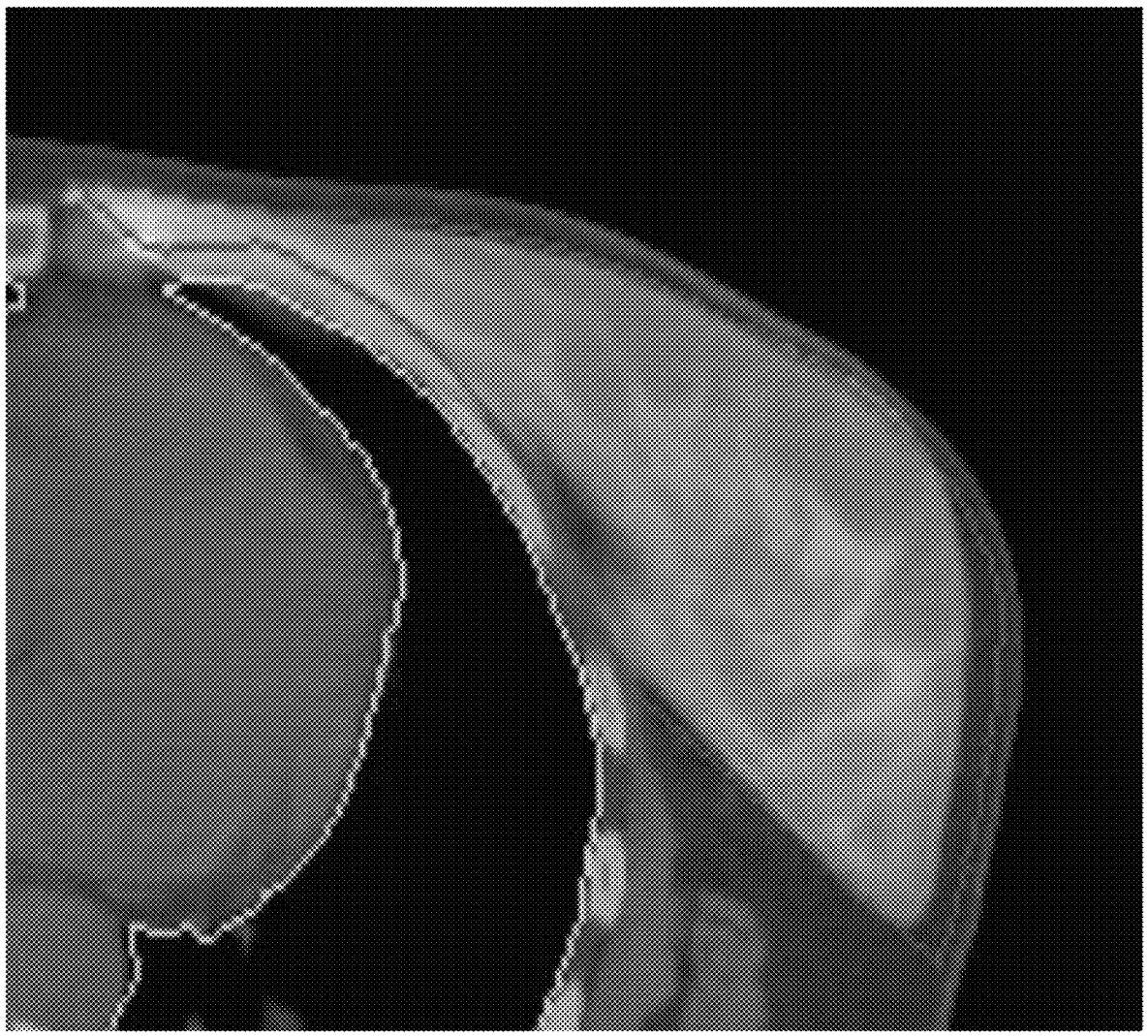
FIG. 2 is a view of balanced delivery of a radiation dose for cancer treatment consistent with certain embodiments of the present invention.

Turning now to FIG. 2, this figure presents a view of balanced delivery of a radiation dose for cancer treatment consistent with certain embodiments of the present invention. In an exemplary embodiment, the system presents a balanced radiation dose optimized for the tissue thickness and contours of a human body part 200. Optimization may be achieved through the arrangement of apertures configured to deliver the radiation dose. The optimization may be governed by the difficulty and cost of reconfiguring multiple leafs and multiple apertures to properly constrain and deliver the radiation dose to a particular tissue or body part.

Figure 3:
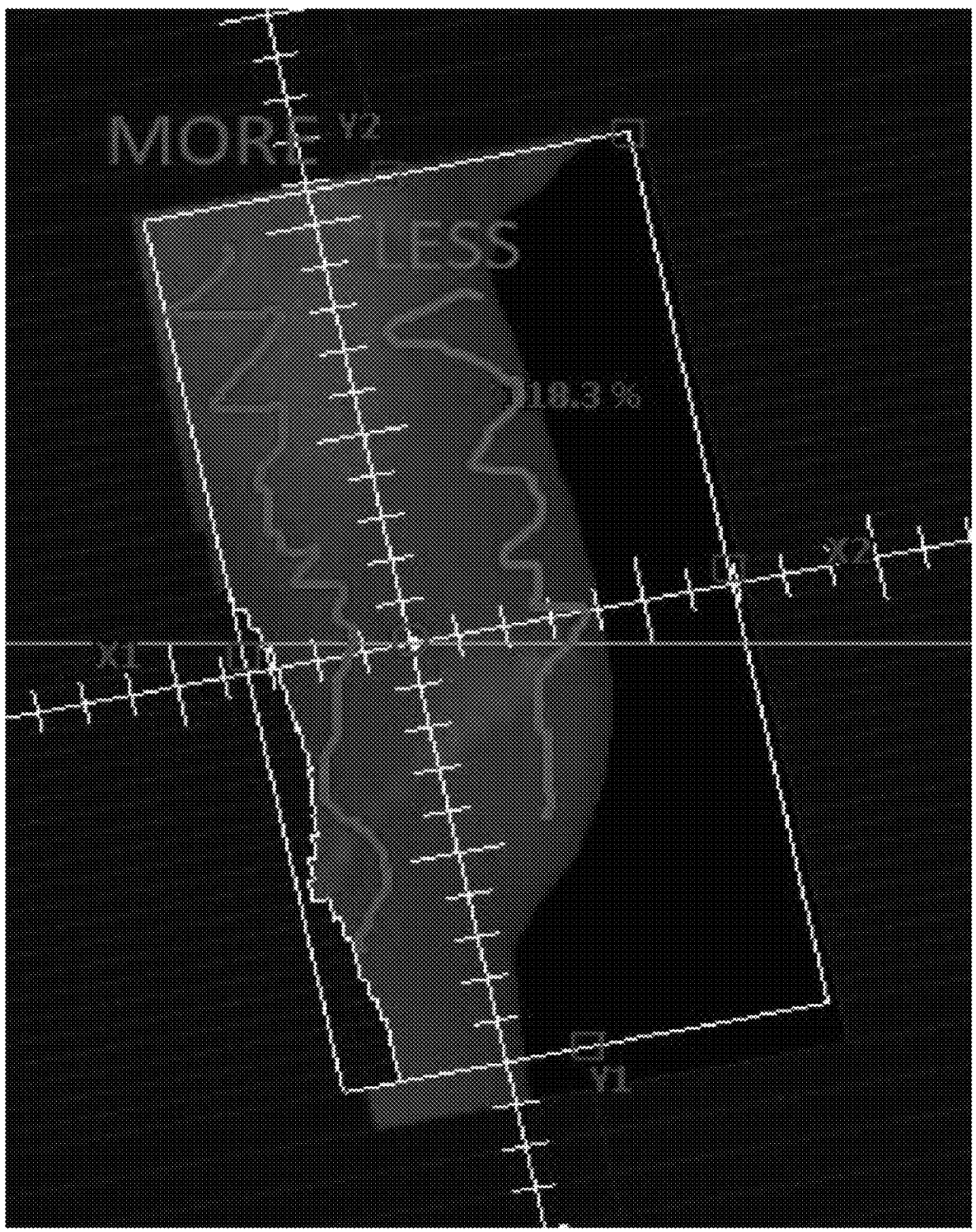
FIG. 3 is a view of dose delivery consistent with certain embodiments of the present invention.

Turning now to FIG. 3, this figure presents a view of dose delivery consistent with certain embodiments of the present invention. In an exemplary embodiment, at 300 this is a view of the areas within a particular targeted tissue to provide the proper radiation dose delivery to a human body part based upon the thickness and contour of the tissue to which the radiation is being delivered.

Figure 4:
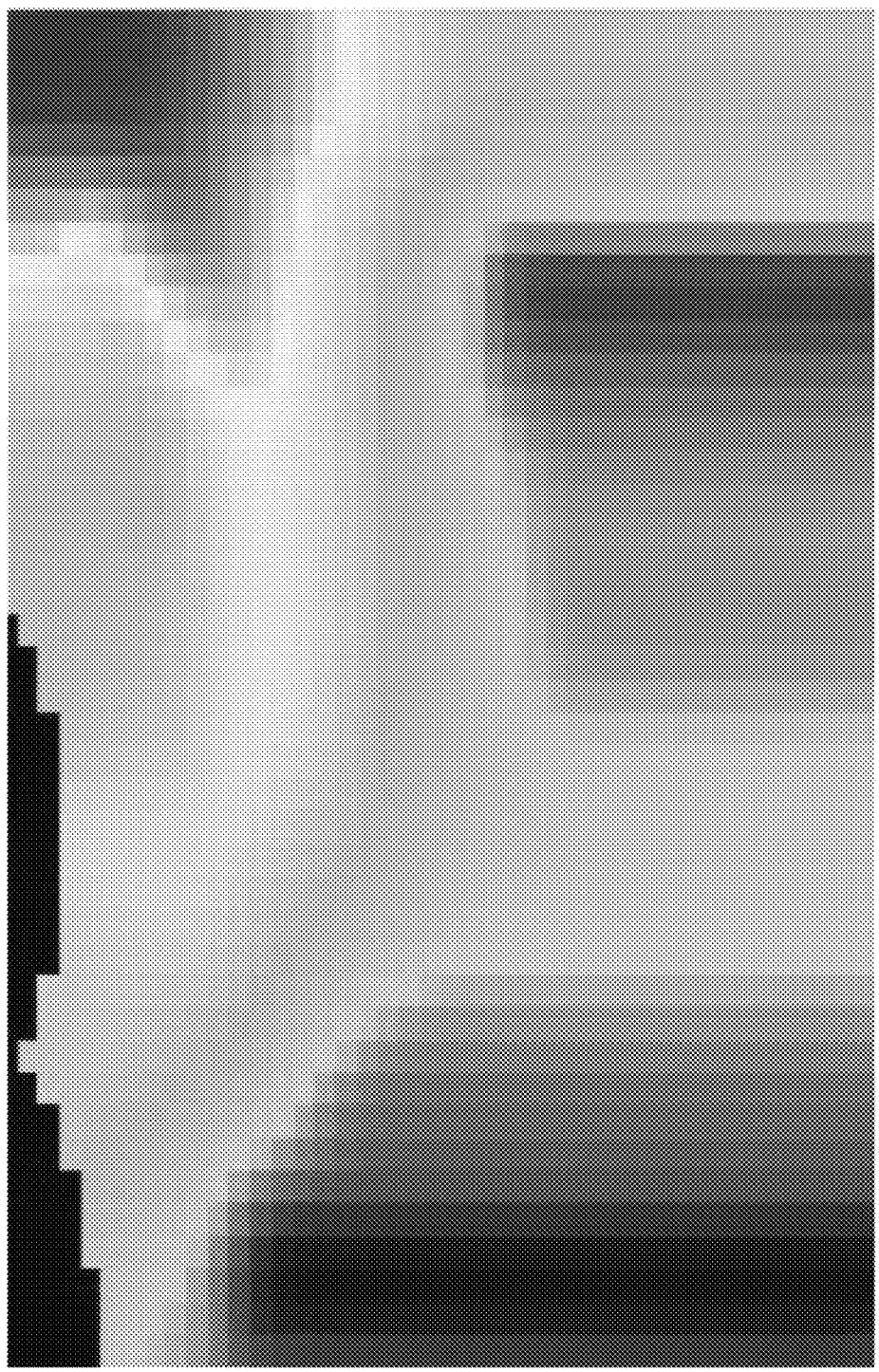
FIG. 4 is a view of a fluence map for dose delivery consistent with certain embodiments of the present invention.

Turning now to FIG. 4, this figure presents a view of a fluence map for dose delivery consistent with certain embodiments of the present invention. In an exemplary embodiment, 400 the fluence map provides a guideline for the dosage deliver over the contour of a body part or tissue.

Figure 5:
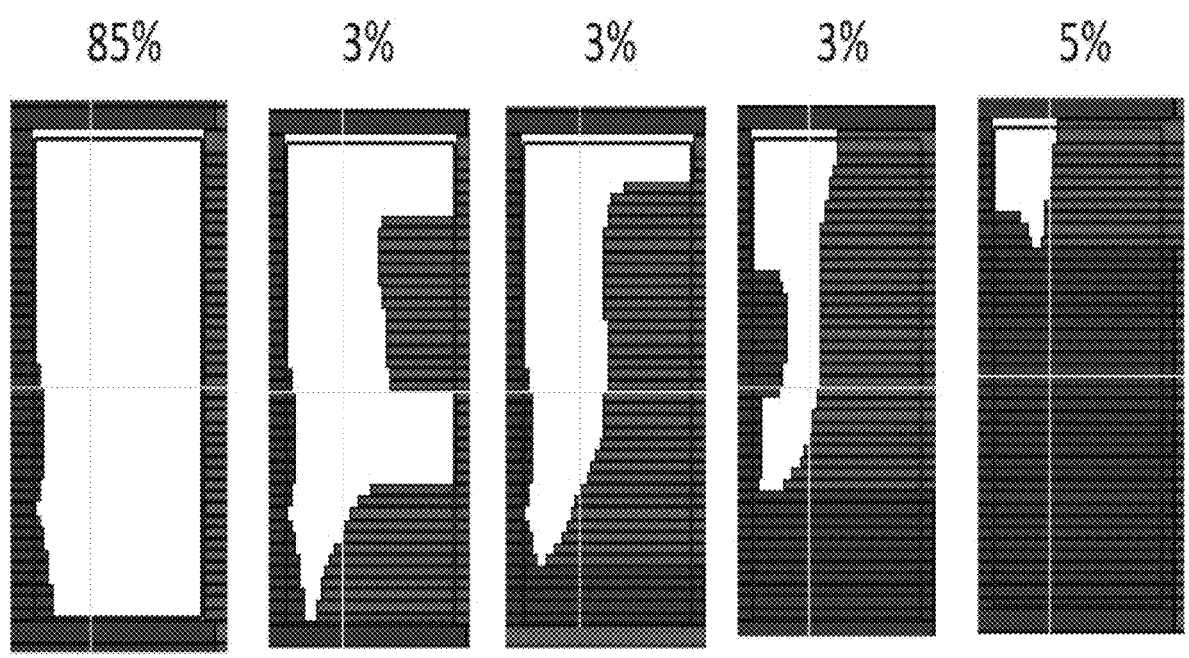
FIG. 5 is a view of positions of apertures for Field-in-Field (FIF) operation consistent with certain embodiments of the present invention.

Turning now to FIG. 5, this figure presents a view of positions of apertures for FIF operation consistent with certain embodiments of the present invention. In an exemplary embodiment, at 500 this figure presents a non-limiting example of a 5-aperture solution for the delivery of a radiation dose in a Field in Field (FIF) radiation delivery system. In this non-limiting example, the radiation doses are delivered in various aperture configurations to provide larger radiation dosages to thicker tissues and smaller radiation dosages to thinner tissues based upon what areas are open or blocked for each aperture configuration. This 5-aperture solution for the FIF system is configured and delivered in a consistent manner with a calculated fluence map created by the system herein described.

Figure 6:
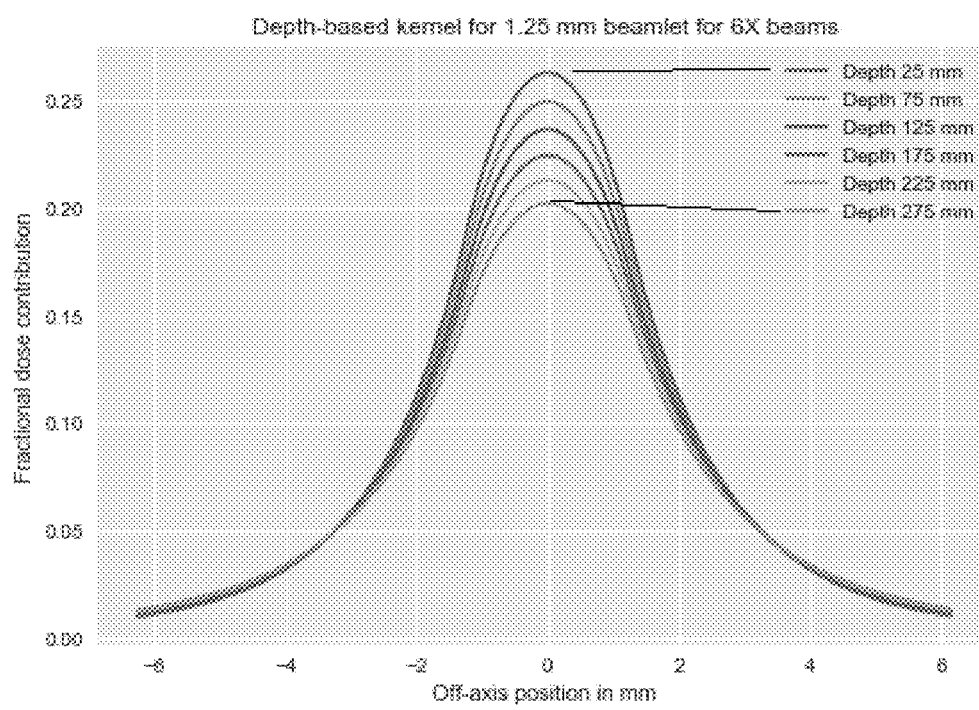
FIG. 6 is a view of a first non-limiting example of a fractional dose delivery map with dose envelope consistent with certain embodiments of the present invention.

Turning now to FIG. 6, this figure presents a view of a first non-limiting example of a dose delivery map consistent with certain embodiments of the present invention. In an exemplary embodiment, at 600 this provides a distribution view for the fractional dose contribution for a 6 MV photon beam setup for distance variations off of a base kernel distance of 1.25 mm. These kernels are used to estimate beamlet-based dose from open field dose. Each beamlet is a variation of depth and off-axis distance as an offset to the base kernel. The dose for a particular aperture is calculated by summing the aggregate effect of all exposed beamlets in the aperture. In an exemplary embodiment, this figure provides the peak dose delivery for each of the apertures defined for the FIF setup to be performed, characterizing the envelop of the dose delivery for the optimized fluence map. A leaf edge leakage penalty is applied to the leaf-covered beamlets, and a falloff term is applied near the leaf tips, both of which are based in the physical characteristics of the leaf material and shape of the leaves. These can be estimated through simulation or through clinical experience.

Figure 7:
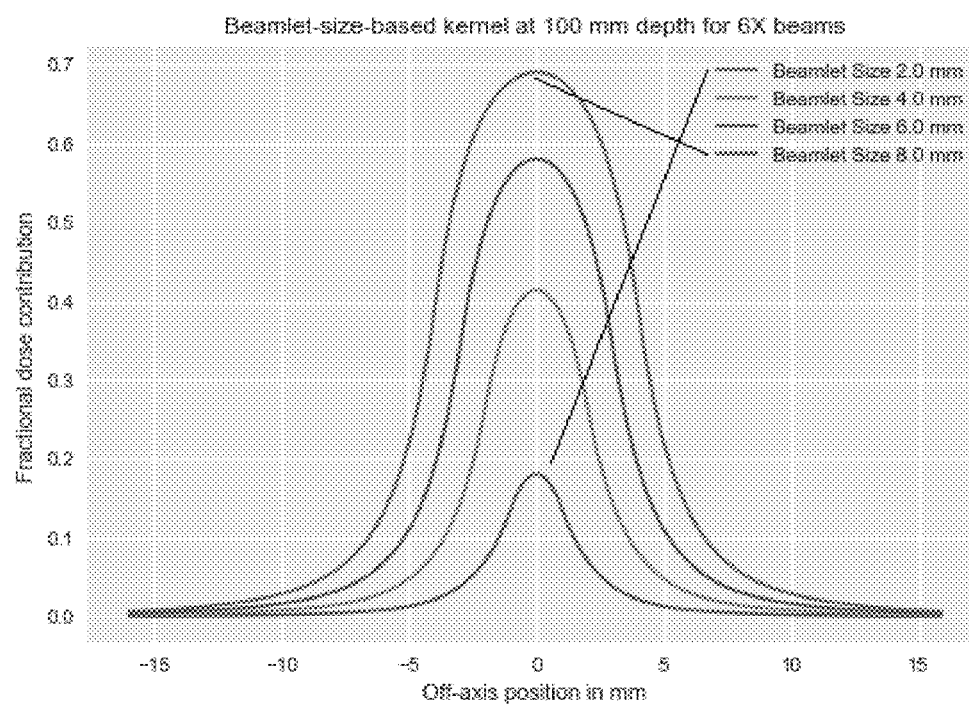
FIG. 7 is a view of a second non-limiting example of a fractional dose delivery map with dose envelope consistent with certain embodiments of the present invention.

Turning now to FIG. 7, this figure presents a view of a second non-limiting example of a dose delivery map consistent with certain embodiments of the present invention. In an exemplary embodiment, at 700 this provides a distribution view for the fractional dose contribution for a 6 MV beam setup for distance variations off of a base kernel distance of 100 mm. These kernels are used to estimate beamlet-based dose from open field dose. Each beamlet is a variation of depth and off-axis distance as an offset to the base kernel. The dose for a particular aperture is calculated by summing the aggregate effect of all exposed beamlets in the aperture. In an exemplary embodiment, this figure provides the peak dose delivery for each of the apertures defined for the FIF setup to be performed, characterizing the envelop of the dose delivery for the optimized fluence map. A leaf edge leakage penalty is applied to the leaf-covered beamlets, and a falloff term is applied near the leaf tips, both of which are based in the physical characteristics of the leaf material and shape of the leaves. These can be estimated through simulation or through clinical experience.

Figure 8:
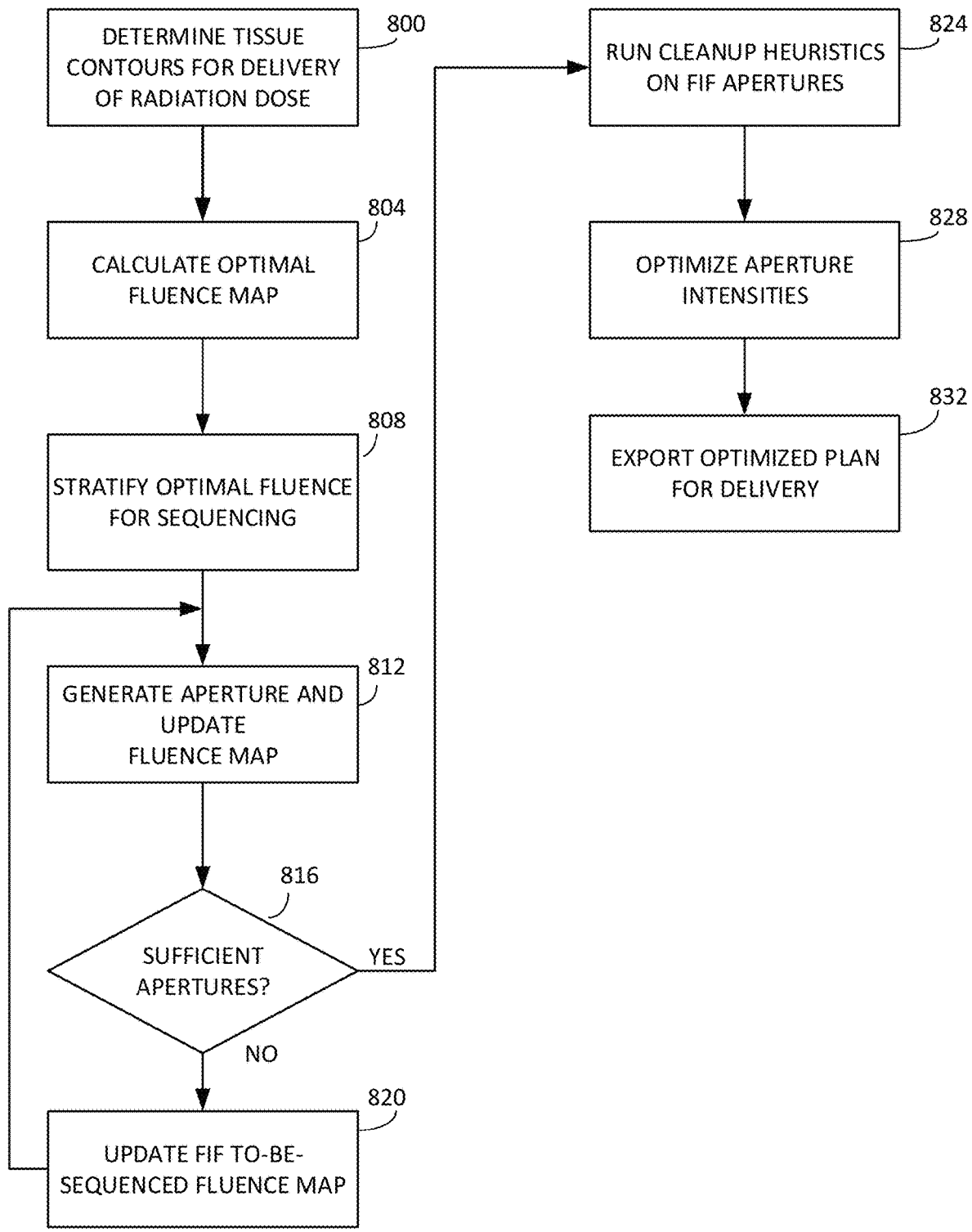
FIG. 8 is a flow diagram for the process for FIF dose delivery with limited apertures consistent with certain embodiments of the present invention.

Turning now to FIG. 8, this figure presents a non-limiting example of a flow diagram for the process for FIF dose delivery with limited apertures consistent with certain embodiments of the present invention. In this embodiment, at 800 the provider must determine the contours of the body part to which a radiation dose is to be delivered. The contours provide an understanding of the areas within the body part having thicker or thinner depths for the tissue of the body part as presented to the radiation dose delivery equipment. At 804, utilizing an FIF-capable delivery system, calculate the fluence map for the optimized delivery of a radiation dose. At 808, determine the fluence stratification to be used to deliver the optimized radiation dose, where the optimized number of apertures may consist of the minimum number of apertures required to deliver the optimized radiation dose. At 812, generate an aperture to best aid in reproducing the stratified fluence pattern and update the aggregate aperture fluence. At 816, If there are insufficient apertures to generate the stratified fluence, then update the to-be-sequenced fluence map for an FIF dose delivery configuration and setup at 820 and return to step 812.

If the optimized radiation dose can be delivered by the FIF delivery equipment using 6 or fewer apertures, run any cleanup heuristics on the aperture settings at 824 and optimize for aperture intensities at 828. The optimized plan can be exported for delivery in 832. Deliver the radiation dose as optimized for the tissues of the identified body part by the FIF radiation delivery equipment utilizing, in a preferred embodiment, 4 to 6 apertures. The radiation dose optimized for the tissues of the identified body part requires that each portion of the tissues of the identified body part receive the radiation dose that is required for each portion regardless of the density of the tissue, the delivery of the radiation dose being homogenous over the entirety of the targeted tissues of the identified body part.

While certain illustrative embodiments have been described, it is evident that many alternatives, modifications, permutations and variations will become apparent to those skilled in the art in light of the foregoing description.

What is claimed is:

1. A system for optimizing radiation dose delivery, comprising:
   one or more apertures for radiation dose delivery;
   a data processor collecting contour measurement information for one or more tissues to receive at least one radiation dose;
   said data processor utilizing said collected contour measurement information to calculate a fluence map for delivery of said radiation dose utilizing said one or more apertures;
   determining a pre-configured maximum number of apertures required to deliver the radiation dose specified by said fluence map, where said number of apertures is less than 10 apertures;
   the data processor determining a minimum amount of radiation allowed to be delivered to a patient for each aperture;
   the data processor determining aperture shapes and desired intensity modulation for delivery of said radiation dose where a pre-configured number of apertures is met and a minimum radiation dose intensity for at least one aperture is defined;
   said data processor aggregating dosimetric effects of all apertures during said determination of aperture shapes and desired intensity modulation;
   said data processor incorporating said aggregated dosimetric effects in said determination of aperture shapes and desired intensity modulation;
   said data processor calculating a peak dose delivery according to said aggregated dosimetric effects for each aperture;
   configuring a Field-in-Field (FIF) radiation delivery device for the said determined apertures;
   said data processor optimizing dose delivery through providing said peak dose delivery for each of said one or more apertures defined for said FIF radiation delivery device;
   delivering an optimized three-dimensional radiation dose distribution to said one or more tissues from said FIF radiation delivery device as specified in said determined number of apertures and said desired intensity modulation.

2. The system of claim 1, where the said pre-configured maximum number of apertures is in the range of 2 to 6 apertures per treatment angle.

3. The system of claim 2, where calculating the pre-configured maximum number of apertures further comprises selecting a number of apertures, testing the resulting delivery of a radiation dose with the selected number of apertures for conformance with said fluence map, and modifying the said number of apertures if the delivered radiation dose is not in conformance with said fluence map.

4. The system of claim 1, where for each of said apertures utilized for delivery of said radiation dose, the radiation dose is determined by applying a leaf edge leakage penalty to leaf-covered beamlets and a falloff term applied near the leaf tips to deliver an optimized dose for said aperture.

5. The system of claim 1, where the contour measurement information of said one or more tissues is utilized in calculating said fluence map to ensure that the delivery of said radiation dose into the one or more tissues is homogenous over the said one or more tissues.

6. The system of claim 1, further comprising utilizing a dose distribution estimate for the one or more tissues given a set of machine parameters for said FIF radiation delivery device.

7. The system of claim 1, further comprising one or more beam intensity determinations consisting of estimating an intensity value for the current aperture and selecting the intensity value that is consistent with replicating said dose distribution from an original fluence map.

8. The system of claim 1, further comprising calculating at least one radiation dose as an estimated dose to be delivered to said one or more tissues given a set of FIF radiation delivery device machine parameters.

9. The system of claim 1, further comprising delivering radiation doses in various aperture configurations to provide larger radiation dosages to thicker tissues and smaller radiation dosages to thinner tissues based upon what areas are open or blocked for each aperture configuration.

10. A method for optimizing radiation dose delivery, comprising:
    configuring one or more apertures for radiation dose delivery;
    collecting contour measurement information for one or more tissues to receive at least one radiation dose;
    calculating, utilizing said collected contour measurement information, a fluence map for delivery of said radiation dose utilizing said one or more apertures;
    determining pre-configured maximum number of apertures required to fulfill the radiation dose specified by said fluence map, where said number of apertures is fewer than 10 apertures;
    determining a minimum amount of radiation allowed to be delivered to a patient for each aperture;
    determining aperture shapes and desired intensity modulation for delivery of said radiation dose where number of apertures and a minimum intensity of said radiation dose for each of said one or more apertures are pre-configured;
    aggregating dosimetric effects of all apertures during said determination of aperture shapes and desired intensity modulation;
    incorporating the aggregated dosimetric effects in said determination of aperture shapes and desired intensity modulation;
    calculating a peak dose delivery according to said aggregated dosimetric effects for each aperture;
    configuring a Field-in-Field (FIF) radiation delivery device for the said number of apertures;
    optimizing dose delivery through providing said peak dose delivery for each aperture defined for said FIF radiation delivery device;
    delivering an optimized radiation dose to said one or more tissues from said FIF radiation delivery device as specified in said number of determined apertures and said desired intensity modulation.

11. The method of claim 10, where the said pre-configured maximum number of apertures is in the range of 2 to 6 apertures.

12. The method of claim 10, where a modified number of apertures is utilized for delivery of said radiation dose.

13. The method of claim 10, where the contour measurement information of said one or more tissues is utilized in calculating said fluence map to ensure that the delivery of said radiation dose into the one or more tissues is homogenous over the said one or more tissues.

14. The method of claim 10, further comprising utilizing a dose distribution estimate for the one or more tissues given a set of machine parameters for said FIF radiation delivery device.

15. The method of claim 10, further comprising one or more beam intensity determinations consisting of estimating an intensity value for the current aperture and selecting the intensity value that is consistent with replicating a dose distribution from an original fluence map.

16. The method of claim 10, further comprising calculating at least one radiation dose as an estimated dose to be delivered to said one or more tissues given a set of FIF radiation delivery device machine parameters.

17. The method of claim 10, further comprising delivering radiation doses in various aperture configurations to provide larger radiation dosages to thicker tissues and smaller radiation dosages to thinner tissues based upon what areas are open or blocked for each aperture configuration.

* * * * *